United States Patent [19]

Lee et al.

[11] 4,304,941

[45] Dec. 8, 1981

[54] METHOD OF PREPARING POLY-SUBSTITUTED ACYLBENZENES

[75] Inventors: Thomas B. K. Lee, White House Station; Gregory M. Jobin, Bridgewater, both of N.J.

[73] Assignee: Hoechst Roussel Pharmaceuticals, Inc., Somerville, N.J.

[21] Appl. No.: 174,399

[22] Filed: Aug. 1, 1980

[51] Int. Cl.$^3$ .............................................. C07C 45/46
[52] U.S. Cl. .................................... 568/322; 568/319; 260/347.8; 549/72; 549/64; 549/63; 549/69; 546/314; 546/315; 546/310; 546/296; 546/297; 546/298
[58] Field of Search ....................... 568/319, 322, 323; 252/449, 455 R; 549/70, 63, 64, 69, 72; 260/347.8; 546/314, 315, 296, 297, 298, 310

[56] References Cited

U.S. PATENT DOCUMENTS

| | | | |
|---|---|---|---|
| 1,995,402 | 3/1935 | Skraup | 568/319 |
| 2,475,567 | 7/1949 | Kosak et al. | 568/319 |
| 2,666,771 | 1/1954 | Zettlemoyer | 568/319 |
| 3,873,622 | 3/1975 | Hetzel | 568/319 |

*Primary Examiner*—Natalie Trousof
*Assistant Examiner*—James H. Reamer
*Attorney, Agent, or Firm*—Jerome Rosenstock

[57] ABSTRACT

A method of preparing substituted acylbenzenes is disclosed. The method comprises reacting selected acylhalides or equivalents with a selected poly-substituted benzene in the presence of an acylating catalyst comprising a clay.

6 Claims, No Drawings

METHOD OF PREPARING POLY-SUBSTITUTED ACYLBENZENES

BACKGROUND OF THE INVENTION

1. Field of the Invention

This invention relates to a method of preparing poly-substituted acylbenzenes and more particularly to synthesizing these acylbenzenes by means of a catalyst comprising a clay.

2. Discussion of the Prior Art

When an acyl halide or equivalent is reacted with 2-bromo-1,3-dimethoxybenzene to form the corresponding acylbenzene it has been found that rearrangement products either predominate or at least are present as major contaminants when usual acylating or Friedel-Craft catalysts are employed. Such rearrangement products involve bromine migration from the 2 to 4 position, e.g.,

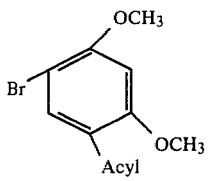

As reported in U.S. Patent Application Ser. No. 157,916, by George M. Shutske and Linda L. Setescak, entitled "A Method of Preparing Poly-substituted Acylbenzenes," filed June 6, 1980, a solid perfluorinated resin sulfonic acid, commercially available from E. I. DuPont de Nemours as Nafion H, is employed as an acylating catalyst in reactions between acyl halides, anhydrides, or mixtures of acids and their anhydrides and 2-bromo-1,3-dimethoxybenzene or 2-bromo-1,3-dihydroxybenzene. Such a perfluorated resin sulfonic acid functions to prevent the formation of rearrangement products when 2-bromo-1,3-dimethoxy or dihydroxybenzene is employed.

SUMMARY OF THE INVENTION

The present invention is directed to a method of preparing polysubstituted acylbenzenes and more particularly to synthesizing the acylbenzenes by means of an acylating catalyst comprising a clay.

The method comprising reacting a first reactant, selected from

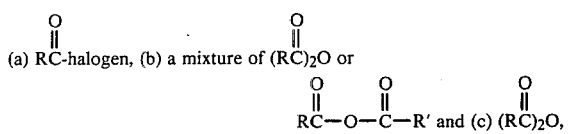

where R is selected from (a') a lower alkyl and (b') a mono or polycyclic aromatic or heteroaromatic having substituents thereon of (X)m and (Y)n, where X and Y are the same or different and are selected from halogen, lower alkyl, lower alkoxy, lower alkylthio, trifluoromethyl and nitro, and m and n are the same or different integers and may vary from 0 to 2, and where R' is selected from a lower alkyl or a polyhaloloweralkyl, with a second reactant, having a structural formula

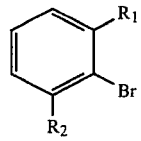

where $R_1$ and $R_2$ are the same or different and are selected from lower alkoxy and hydroxy, in the presence of an acylating catalyst comprising a clay.

DETAILED DESCRIPTION

The present invention is described primarily in terms of acylating 2-bromo-1,3-dimethoxybenzene to form a substituted benzophenone without essentially forming a contaminating rearrangement acylating product; however, it will be understood that such description is exemplary only and is for purposes of exposition and not for purposes of limitation. It will be readily appreciated that the inventive concept described is equally applicable to acylating 2-bromo-1,3-dimethoxybenzene or 2-bromo-1,3-dihydroxybenzene with any acylhalide or equivalent such as an acylanhydride or mixture of such an anhydride and its corresponding acid.

A first reactant selected from

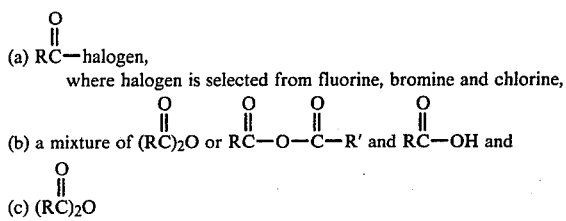

is selected. R is selected from a lower alkyl and a mono or polycyclic aromatic having a substituent thereon of (X)m and (Y)n, where X and Y are the same or different and are selected from halogen, lower alkyl, lower alkoxy, lower alkylthio, trifluoromethyl and nitro, and m and n are the same or different integers and may vary from 0 to 2, and R' is selected from a lower alkyl or a polyhaloloweralkyl, e.g.,

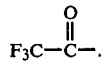

By the term "lower" is meant a substituent having from 1 to 6 carbon atoms. In the case where the desired product is a benzophenone, a benzoyl halide of the formula

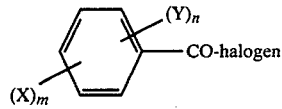

may be selected. Alternatively if a different acylbenzene is desired an appropriate first reactant is selected wherein R is lower alkyl, or another appropriately substituted aromatic group or a heteroaromatic group, including but not limited to naphthyl, e.g.,

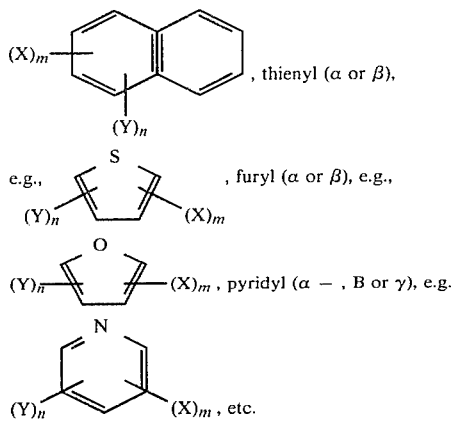, thienyl (α or β), e.g., 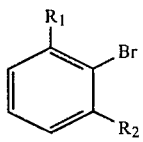, furyl (α or β), e.g., (Y)ₙ—[O]—(X)ₘ, pyridyl (α — , β or γ), e.g.

[N-ring image], etc.

A second reactant comprising a compound of the structure $$\underset{R_2}{\underset{\displaystyle\bigcirc}{R_1}}\text{Br}$$

where $R_1$ and $R_2$ are the same or different and selected from lower alkoxy and hydroxy, e.g., 2-bromo-1,3-methoxybenzene, is selected.

A suitable acylating catalyst is selected. A suitable catalyst comprises a suitable clay. Such a suitable clay is selected from a montmorillonite having an approximate formula of $R_{0.33}{}^+$ (Al, Mg)$_2$Si$_4$O$_{10}$(OH)$_2$.nH$_2$O where R+ in natural material includes one or more of the cations Na+, K+, Mg$^{2+}$, Ca$^{2+}$, and Fe$^{3+}$. A preferred montmorillonite is an acidic montmorillonite, such as an acidic montmorillonite clay catalyst supplied by United Catalysts, Inc., Louisville, Kentucky, and designated as "K-10" catalyst, whose chemical constituents are silicon dioxide, aluminum oxide, iron (III) oxide, magnesium oxide, calcium oxide, sodium oxide and potassium oxide.

The first reactant, the second reactant, the suitable clay and a suitable solvent, are combined and reacted under the usual Friedel-Crafts reaction conditions. Typically the reactant and catalyst are heated to reflux for a sufficient period of time to achieve the desired acylation, e.g., 22–40 hours.

Surprisingly and unexpectedly, the use of the clay yields the desired product, 4-acyl-2-bromo-1,3-dialkoxy- or dihydroxybenzene, which is free from contamination or formation of significant rearrangement products. This is a surprising and unexpected result since with the usual Friedel-Crafts acylation catalysts, e.g., Lewis acids such as SnCl$_4$, ZnCl$_2$, AlCl$_3$, etc., such rearrangement products are obtained and may often predominate. Such rearrangement products, it is believed, occur because the usual Friedel-Crafts catalysts promote metathesis of the starting material such as 2-bromo-1,3-dimethoxybenzene to yield 4,6-dibromo-1,3-dimethoxybenzene,2,4-dimethoxybromobenzene, and 1,3-dimethoxybenzene. It is this "rearranged starting material" which reacts with the requisite acylating agents to give poor yields of the desired acyl-2-bromo-1,3-dimethoxybenzenes. Surprisingly and unexpectedly the catalysts of the instant process do not cause such rearrangements but promote instead only the desired acylation.

EXAMPLE 1

3-Bromo-2,4-dimethoxy-2'-fluorobenzophenone

A mixture of 3.26 g (0.015 mole) 2,6-dimethoxy-bromobenzene (2-bromo-1,3-dimethoxybenzene), 2.26 ml (0.0189 mole) 2-fluorobenzoyl chloride and 0.75 g Montmorillonite K-10 Clay [an acidic montmorillonite clay commercially obtained from United Catalysts, Inc.] (dried at 180° C. in vacuo for 18 hours) in 15 ml of 1,2-dichloromethane is refluxed for 18 hours. The mixture is cooled to 70° C. and 0.25 g of additional K-10 clay is added. The reaction is maintained at reflux for another 20 hours. After cooling to room temperature, the clay is removed by filtration. The filtrate is concentrated under reduced pressure to yield 4.87 g of the crude product as an oil. This crude product is recrystallized from 10 ml of isopropyl alcohol to give 3.34 g (65.6%) of white crystals, m.p. 93°–95° C. which correspond by m.p., NMR, MS IR to an authentic sample.

As reported in U.S. Patent Application Ser. No. 157,916, by Gregory M. Shutske and Linda L. Setescak, entitled "A Method of Preparing Poly-substituted Acylbenzenes," filed on June 6, 1980, when Friedel-Crafts agents, such as SnCl$_4$, ZnCl$_4$, AlCl$_3$, BBr$_3$, and TiCl$_4$, are employed, either a desired reaction product is not obtained or a mixture of 3-bromo-2,4-dimethoxy-2'-fluorobenzophenone [desired product], 5-bromo-2,4-dimethoxy-2'-fluorobenzophenone [undesired rearrangement product] and/or the various rearranged starting material as heretofore described is obtained.

The following are comparative prodedures as reported in the above identified U.S. Patent Application for the various catalysts employed which graphically illustrate the surprising and unexpected superiority not only of the perfluorosulfonic acid polymer catalysts reported therein, but also of the clay catalyst of the present invention.

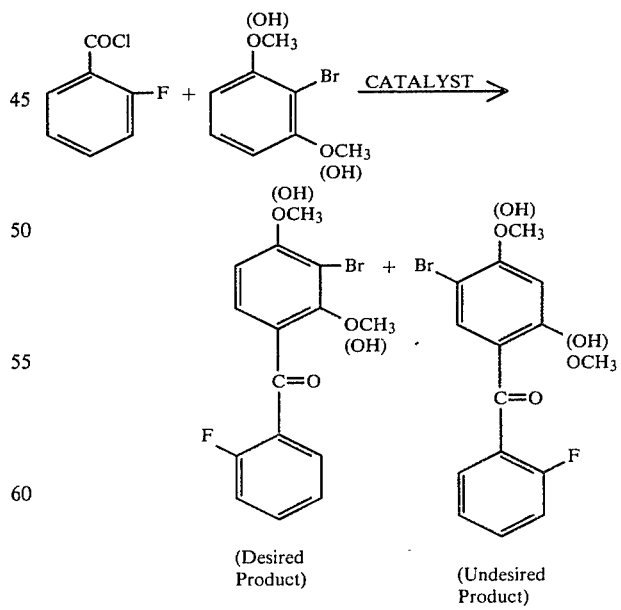

[a] SnCl$_4$

2-Fluorobenzoyl chloride (1.58 g; 0.010 mole) is dissolved in 15 ml of 1,2-dichloroethane at ice bath temperature. Stannic chloride (2.58 g; 0.010 mole) is added and the reaction is stirred 5 minutes, after which 2-bromo-1,3-dimethoxybenzene is added (2.17 g; 0.010 mole) in 3 ml of 1,2-dichloroethane. After 2 hours, the following mixture of products is obtained, as analyzed by the technique of mass spectromotry/gas chromatography; 2-bromo-1,3-dimethoxybenzene (9.5%), 4-bromo-1,3-dimethoxybenzene (trace), 4,6-dibromo-1,3-dimethoxybenzene (8.0%), 2'-fluoro-2,4-dimethoxybenzophenone (11.1%), 3-bromo-2'-fluoro-2,4-dimethoxybenzophenone (22.9%), 5-bromo-2'-fluoro-2,4-dimethoxybenzophenone (13.7%).

[b] ZnCl₂

2-bromo-1,3-dimethoxybenzene (2.17 g; 0.010 mole) is dissolved in 7 ml of dichloromethane and freshly fused zinc chloride 1.36 g; 0.010 mole) is added. After stirring 15 minutes at room temperature, 2-fluorobenzoyl chloride (1.58 g; 0.010 mole) is added. After stirring 3 days at room temperature, the following mixture is obtained, as analyzed by gas chromatography; 2-bromo-1,3-dimethoxybenzene (9%), 4-bromo-1,3-dimethoxybenzene (trace); 4,6-dibromo-1,3-dimethoxybenzene (7%); 2'-fluoro-2,4-dimethoxybenzophenone (22%); 3-bromo-2'-fluoro-2,4-dimethoxybenzophenone (4%), 5-bromo-2'-fluoro-2,4-dimethoxybenzophenone (31%).

[c] AlCl₃

2-bromo-1,3-dimethoxybenzene (217 g; 1.0 mole) and 2-fluorobenzoyl chloride (158 g; 1.0 mole) are dissolved in 1,2-dichlorothane and aluminum chloride (133 g; 1.0 mole) is added slowly. The reaction mixture is refluxed for 2 hours and then worked up with 5% hydrochloric acid. In this way a 1:2 mixture of 5-bromo-2'-fluoro-2-hydroxy-4-methoxybenzophenone and 3-bromo-2'-fluoro-2-hydroxy-4-methoxybenzophenone is obtained, as indicated by nuclear magnetic resonance (NMR). A quantity of this mixture is separated by preparative high pressure liquid chromatography into its two components, 5-bromo-2'-fluoro-2-hydroxy-4-methoxybenzophenone, m.p. 127°–129° C. and 3-bromo-2'-fluoro-2-hydroxy-4-methoxybenzophenone, m.p. 137°–139° C.

[d] BBr₃

2-bromo-1,3-dimethoxybenzene (4.34 g; 0.020 mole) is dissolved in 15 ml of dichloromethane and 2-fluorobenzoyl chloride (3.16 g; 0.020 mole) is added. This mixture is chilled in an ice bath as boron tribromide is added (3.10 g; 0.020 mole). The reaction is brought to reflux and refluxed for 16 hours. Thin layer chromatography shows qualitatively an equal mixture of 5-bromo-2'-fluoro-2-hydroxy-4-methoxybenzophenone and 3-bromo-2'-fluoro-2-hydroxy-4-methoxybenzophenone.

[e] TiCl₄

2-bromo-1,3-dimethoxybenzene (2.17 g; 0.010 mole) and 2-fluorobenzoyl chloride (1.58 g; 0.010 mole) are dissolved in 15 ml of 1,2-dichloroethane at −5° C. and titanium tetrachloride (1.89 g; 0.010 mole) is added. After 2.5 hours gas chromatography shows that 2-bromo-1,3-dimethoxybenzene is entirely consumed and the following mixture of products is present: 4,6-dibromo-1,3-dimethoxybenzene (4%); 2'-fluoro-2,4-dimethoxybenzophenone (10%); 3-bromo-2'-fluoro-2,4-dimethoxybenzophenone (46%); 5-bromo-2'-fluoro-2,4-dimethoxybenzophenone (34%).

Also reported in the above-identified Application is the effect that usual Friedel-Crafts catalysts have on the starting 2-bromo-1,3-dimethoxybenzene. In this regard, 2.17 gm (0.010 mole) of this material is dissolved in 15 ml of 1,2-dichloroethane and ferric chloride (1.62 g; 0.010 mole) is added. After 30 minutes at room temperature gas chromatography shows that 2-bromo-1,3-dimethoxybenzene is almost completely consumed and a mixture of 2,4-dimethoxybromobenzene, 1,3-dimethoxybenzene, and 4,6-dibromo-1,3-dimethoxybenzene is in its place.

We claim:

1. A method of preparing a poly-substituted acylbenzene having a structural formula of

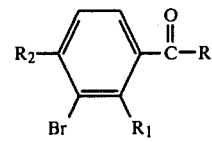

where R₁ and R₂ are the same or different and are selected from the group consisting of lower alkoxy and hydroxy, R is selected from the group consisting of (a) a lower alkyl, and (b) an aryl selected from phenyl, naphthyl, α-thienyl, β-thienyl, α-furyl, β-furyl, α-pyridyl, β-pyridyl and γ-pyridyl, each having substituents thereon of (X)ₘ and (Y)ₙ where X and Y are the same or different and are selected from the group consisting of halogen, lower alkyl, lower alkoxy, lower alkylthio, trifluoromethyl and nitro, and m and n are the same or different integers and may vary from φ to 2, which comprises reacting a first reactant selected from the group consisting $$\text{of } \overset{O}{\underset{\parallel}{RC}}\text{—halogen, a mixture of } (RC)_2\phi \text{ or } \overset{O}{\underset{\parallel}{RC}}\text{—}\phi\text{—}\overset{O}{\underset{\parallel}{C}}\text{—}R^1 \text{ and}$$

$$\overset{O}{\underset{\parallel}{RC}}\text{—OH and } (RC)_2\phi,$$

where R is defined above and R¹ is selected from a lower alkyl and a polyhaloloweralkyl, with a second reactant having a formula of

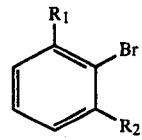

where R₁ and R₂ are as defined above, in the presence of an acylating agent comprising a montmorillonite clay.

2. The method as defined in claim 1 wherein said clay comprises an acidic montmorillonite clay.

3. The method as defined in claim 1 where R is

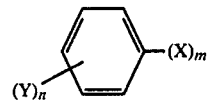

and X, Y, m and n are as defined.

4. The method as defined in claim 1 wherein a 2-fluorobenzoyl halide is reacted with 2-bromo-1,3-dimethoxybenzene to form a reaction product of

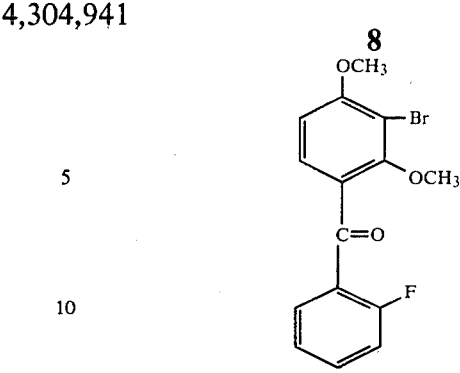
which is essentially free of a rearrangement product.
5. The method as defined in claim 1 wherein a 2-fluorobenzoyl halide is reacted with 2-bromo-1,3-dimethoxybenzene to form 3-bromo-2,4-dimethoxy-2'-fluorobenzophenone.
6. The method as defined in claim 5 wherein said acylating catalyst comprises an acidic montmorillonite clay.
* * * * *

UNITED STATES PATENT AND TRADEMARK OFFICE
CERTIFICATE OF CORRECTION

PATENT NO. : 4,304,941
DATED : December 8, 1981
INVENTOR(S) : Lee et al.

It is certified that error appears in the above—identified patent and that said Letters Patent is hereby corrected as shown below:

Column 1, line 40: "perfluorated" should be --perfluorinated--

" 1, " 58: insert --and $R\overset{O}{C}$-OH-- bewteen "$R\overset{O}{C}$-O-$\overset{O}{C}$-R'" AND "and (c) $(R\overset{O}{C})_2O$,"

" 3, " 13: "B" should be --$\beta$--

" 3, " 35: "$R_{0.33}^+$" should be --$R^+_{0.33}$--

" 4, " 34: "prodedures" should be --procedures--

" 5, " 29: "1,2-dichlorothane" should be --1,2-dichloroethane--

Claim 3: "where" should be --wherein--

Signed and Sealed this

Thirtieth Day of March 1982

[SEAL]

Attest:

GERALD J. MOSSINGHOFF
Attesting Officer    Commissioner of Patents and Trademarks